(12) United States Patent  
Czeizler et al.

(10) Patent No.: US 12,138,483 B2  
(45) Date of Patent: Nov. 12, 2024

(54) METHOD AND APPARATUS FOR RADIATION TREATMENT PLAN RISK ASSESSMENT

(71) Applicant: Siemens Healthineers International AG, Steinhausen (CH)

(72) Inventors: Elena Czeizler, Helsinki (FI); Esa Kuusela, Espoo (FI); Maria Isabel Cordero Marcos, Espoo (FI); Hannu Laaksonen, Espoo (FI); Jan Schreier, Helsinki (FI)

(73) Assignee: Siemens Healthineers International AG, Steinhausen (CH)

( * ) Notice: Subject to any disclaimer, the term of this patent is extended or adjusted under 35 U.S.C. 154(b) by 622 days.

(21) Appl. No.: 16/836,411

(22) Filed: Mar. 31, 2020

(65) Prior Publication Data

US 2021/0299476 A1    Sep. 30, 2021

(51) Int. Cl.
| | |
|---|---|
| *A61N 5/10* | (2006.01) |
| *G06T 7/00* | (2017.01) |
| *G06T 7/11* | (2017.01) |
| *G06T 7/73* | (2017.01) |
| *G06T 9/00* | (2006.01) |

(52) U.S. Cl.
CPC ......... *A61N 5/1071* (2013.01); *A61N 5/1031* (2013.01); *G06T 7/0012* (2013.01); *G06T 7/11* (2017.01); *G06T 7/73* (2017.01); *G06T 9/002* (2013.01); *G06T 2207/10116* (2013.01); *G06T 2207/20081* (2013.01); *G06T 2207/20084* (2013.01); *G06T 2207/20112* (2013.01); *G06T 2207/30004* (2013.01)

(58) Field of Classification Search
CPC .. A61N 5/1071; A61N 5/1031; G06T 7/0012; G06T 7/11; G06T 7/73; G06T 9/002; G06T 2207/10116; G06T 2207/20081; G06T 2207/20084; G06T 2207/20112; G06T 2207/30004; G06T 2200/24; G06T 2207/30096; G06T 2207/10081

See application file for complete search history.

(56) References Cited

U.S. PATENT DOCUMENTS

| | | | |
|---|---|---|---|
| 8,262,555 B2 * | 9/2012 | Jervis | A61N 5/1015 600/3 |
| 9,192,782 B1 * | 11/2015 | Grimm | A61N 5/1031 |
| 11,848,106 B1 * | 12/2023 | Wood | G16H 50/30 |

(Continued)

OTHER PUBLICATIONS

Zhen, Xin et al., Deep Convolutional Neural Network with Transfer Learning for Rectum Toxicity Prediction in Cervical Cancer Radiotherapy: A Feasibility Study; Phys. Med. Biol. 62 (2017), pp. 8246-8263.

(Continued)

*Primary Examiner* — Maurice L. McDowell, Jr.

(74) *Attorney, Agent, or Firm* — Fitch, Even, Tabin & Flannery LLP

(57) ABSTRACT

A control circuit accesses patient information including anatomical image information of the patient, segmentation information corresponding to the anatomical image information, and a dose map for the radiation treatment plan. The control circuit then generates at least one organ-specific three-dimensional risk map as a function of the patient information and presents that risk map to a user via a display.

20 Claims, 3 Drawing Sheets

(56) References Cited

U.S. PATENT DOCUMENTS

| | | | | |
|---|---|---|---|---|
| 2012/0020460 | A1* | 1/2012 | Witten | A61N 5/103 |
| | | | | 378/65 |
| 2013/0083004 | A1* | 4/2013 | Nord | A61N 5/1031 |
| | | | | 345/419 |
| 2016/0256711 | A1* | 9/2016 | Pappas | A61N 5/1075 |
| 2017/0177812 | A1* | 6/2017 | Sjölund | G16H 20/40 |
| 2019/0333623 | A1* | 10/2019 | Hibbard | A61N 5/1031 |
| 2020/0069973 | A1* | 3/2020 | Lou | G06N 7/005 |
| 2020/0075148 | A1* | 3/2020 | Nguyen | G16H 50/30 |
| 2020/0155868 | A1* | 5/2020 | Yuan | G06N 3/08 |
| 2020/0254277 | A1* | 8/2020 | Eriksson | G06N 3/08 |
| 2020/0289847 | A1* | 9/2020 | Sjölund | G06N 20/00 |
| 2021/0158929 | A1* | 5/2021 | Sjolund | A61N 5/1038 |

OTHER PUBLICATIONS

Mayo, Charles et al., Radiation Associated Brainstem Injury; Int. J Radiat Oncol Biol Phys. Mar. 1, 2010; 76(3 Suppl): S36-S41. doi:10.1016/j.ijrobp.2009.08.078; 10 pages.

Selvaraju, Ramprasaath R et al., Grad-CAM: Visual Explanations from Deep Networks Via Gradient-Based Localization; International Journal of Computer Vision (IJCV); arXiv:1610.02391v4; Dec. 3, 2019; 23 pages.

Ibragimov, Bulat et al.; Deep 3D Dose Analysis for Prediction of Outcomes After Liver Stereotactic Body Radiation Therapy; Medical Image Computing and Computer Assisted Intervention—MICCAI 2018: 21st International Conference, 2018, pp. 684-692; Sep. 26, 2018.

* cited by examiner

METHOD AND APPARATUS FOR RADIATION TREATMENT PLAN RISK ASSESSMENT

TECHNICAL FIELD

These teachings relate generally to the use of radiation as a therapeutic treatment and more specifically to the assessment of adverse risks corresponding to treatment outcomes associated with a given radiation treatment plan.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

The aforementioned treatment results are typically represented as a particular amount of radiation (often expressed in grays (Gy's) where one Gy is defined as the absorption of one joule of radiation energy per kilogram of matter). While a helpful representation, such quantified results do not intuitively inform the user with respect to certain potential categorical risks to the patient. For example, knowing that a particular organ-at-risk will receive 25 Gy during treatment does not necessarily ensure that the technician will understand or recognize whether that places this particular organ at some risk of a particular categorical adverse result such as bleeding. In some cases there are guidelines available that will correlate a particular dosage level to a particular adverse effect, but to the extent that such guidelines might be available in a given application setting, those guidelines treat the organ as an amorphous whole. In fact, some organs have subregions that can be more sensitive than other parts of the organ to particular radiation dosages, and the applicant has determined that treating the organ as being similarly affected in all portions thereof by a given radiation dosage is unrealistic and therefore sometimes leads to unhelpful or even misleading results.

Accordingly, present technology fails to a greater or lesser extent to more fully and completely inform a radiation treatment plan technician regarding potential adverse outcome risks.

BRIEF DESCRIPTION OF THE DRAWINGS

The above needs are at least partially met through provision of the method and apparatus for radiation treatment plan risk assessment described in the following detailed description, particularly when studied in conjunction with the drawings, wherein.

Figure 1:
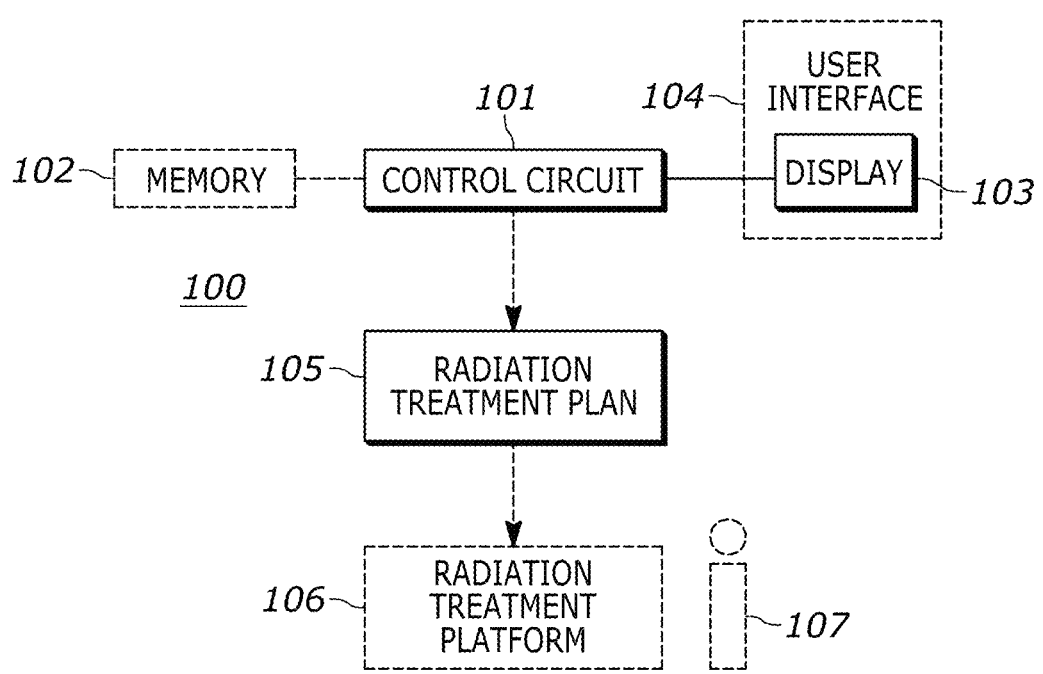
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments facilitate assessing risks associated with a radiation treatment plan for a particular patient. A control circuit accesses patient information including anatomical image information of the patient, segmentation information corresponding to the anatomical image information, and a dose map for the radiation treatment plan. By one approach the control circuit then generates at least one organ-specific three-dimensional risk map as a function of the patient information and presents that risk map to a user via a display. By another approach, in lieu of the foregoing or in combination therewith, the control circuit may generate a general three-dimensional risk map for anatomical structures other than organs such as, for example, bones.

The aforementioned segmentation information can serve to identify discrete patient organs (including one or more organs at risk and/or treatment volumes). In lieu of the foregoing or in combination therewith the segmentation information may serve to identify discrete anatomical structures other than organs.

By one approach the control circuit generates the aforementioned organ-specific three-dimensional risk map as a function of the patient information by employing a neural network such as, but not limited to, a convolutional neural network. By one approach the control circuit employs two or more different neural networks. For example, the control circuit may employ both a convolutional neural network and a fully-connected neural network. By one approach, if desired, the neural network can further comprise, at least in part, a recurrent neural network.

By one approach the neural network serves, at least in part, to extract features from the patient information. The neural network can be trained, for example, for at least one of a segmentation task and an auto-encoding task. By one approach the neural network can serve to predict the overall probability for a certain side effect. In that case the same neural network can then used to identify from which area of the input CT imagery this risk is originating from. The ordinarily-skilled person will appreciate that the neural network can therefore utilize transfer learning (in which case the already-trained network can be used as-is to extract general features or the network can be finetuned to, for example, extract features that are particularly specific to the present task) or, if desired, the neural network can be trained from scratch to predict the required outcome and risk map starting directly from the patient images (and hence without splitting the solution into feature selection followed by outcome prediction).

By one approach the control circuit generates the organ-specific (and/or other patient structure(s) of interest) three-dimensional risk map by predicting at least one treatment outcome as a function of a set of defined treatment outcomes and features that are extracted from the patient information. A neural network may serve in these regards or, if desired, the control circuit may utilize a non-neural network platform such as, for example, a random decision forest platform.

By one approach the organ-specific three-dimensional risk map visually highlights areas in a corresponding patient organ having a higher probability for an undesirable outcome prediction for the patient when administering the radiation treatment plan. This may comprise, for example, visually highlighting one or more separate and discrete volumes within the corresponding patient organ. These separate and discrete volumes may be highlighted differently to indicate differing degrees of risk for an undesirable outcome.

These and other benefits may become clearer upon making a thorough review and study of the following detailed description. Referring now to the drawings, and in particular to FIG. 1, an illustrative apparatus 100 that is compatible with many of these teachings will now be presented.

In this example the apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

By one optional approach the control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to the aforementioned anatomical image, segmentation, and dose map information, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

In this illustrative example the control circuit 101 operably couples to at least one display 103 such as, but not limited to, a touch-screen display. In many application settings it will be helpful for this display 103 to be a full color display though these teachings will accommodate other approaches in these regards.

By one optional approach this display 103 can be part of a more fully-featured user interface 104. This user interface 104 can comprise any of a variety of user-input mechanisms (such as, but not limited to, keyboards and keypads, cursor-control devices, touch-sensitive displays, speech-recognition interfaces, gesture-recognition interfaces, and so forth) and/or additional user-output mechanisms (such as, but not limited to, audio transducers, printers, and so forth) to facilitate receiving information and/or instructions from a user and/or providing information to a user.

This application setting presumes the availability of a radiation treatment plan 105 that likely though not necessarily constitutes an optimized radiation treatment plan for administering therapeutic radiation via a particular radiation treatment platform 106 to a particular patient 107.

These teachings are generally applicable for use with any of a wide variety of radiation treatment platforms 106. In a typical application setting the radiation treatment platform 106 will include an x-ray source. The x-ray source can comprise, for example, a radio-frequency (RF) linear particle accelerator-based (linac-based) x-ray source, such as the Varian Linatron M9. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) and high energy electrons. A typical radiation treatment platform 106 may also include one or more support surfaces (such as a couch) to support the patient 107 during the treatment session, a gantry or other mechanism to permit selective movement of the x-ray source, and one or more components (such as jaws, multi-leaf collimators, and so forth) to provide selective beam shaping and/or beam modulation as desired. As the foregoing elements and systems are well understood in the art, further elaboration in these regards is not provided here except where otherwise relevant to the description.

Figure 2:
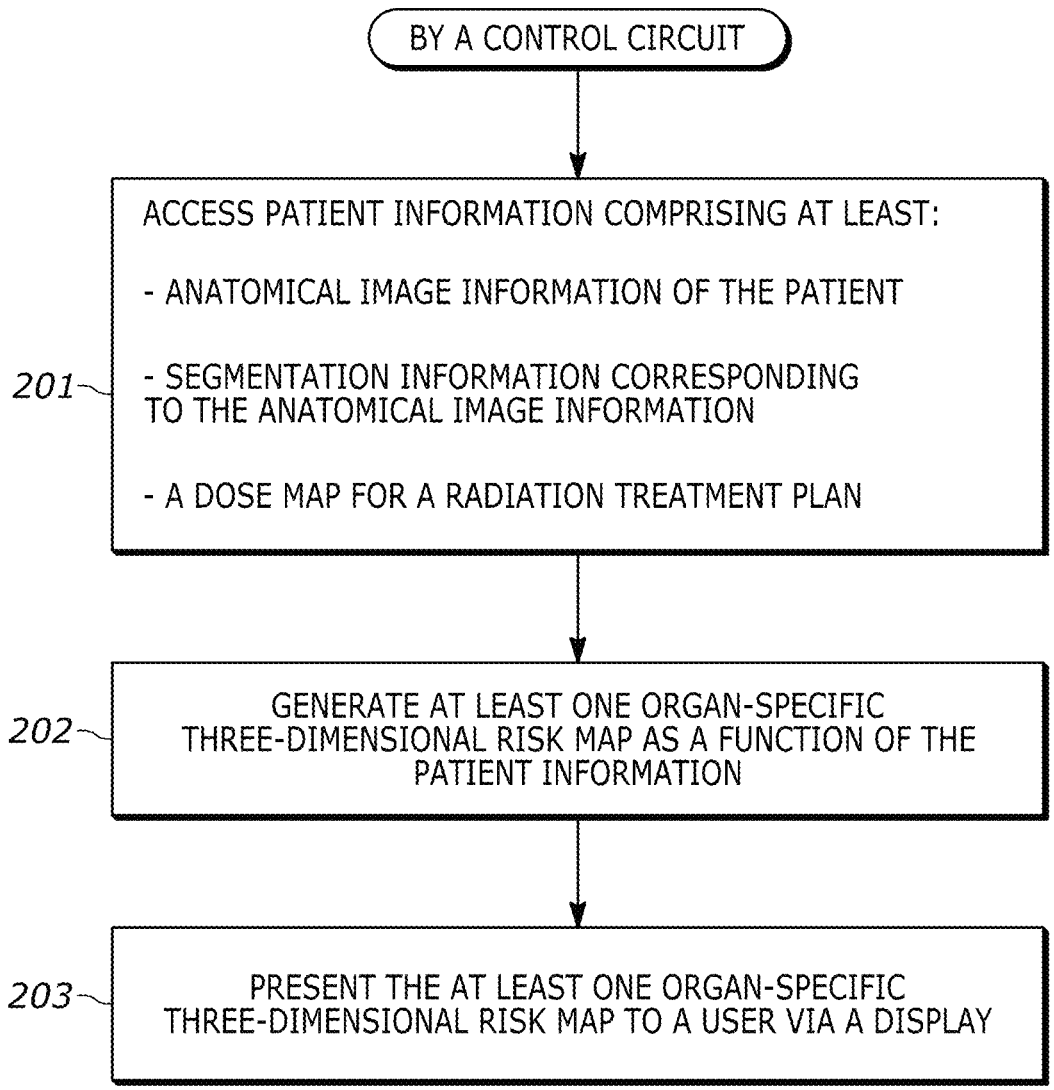
FIG. 2 comprises a flow diagram as configured in accordance with various embodiments of these teachings.

Referring now to FIG. 2, and with continued reference to FIG. 1, a process 200 to facilitate assessing risks associated with a radiation treatment plan 105 for a particular patient 107 will be described. For the sake of an illustrative example this description presumes that the above-described control circuit 101 carries out the steps, actions, and functions of this process 200.

At block 201 the control circuit 101 accesses patient information (for example, by retrieving such information from the aforementioned memory 102). In this example, that patient information includes, but is not limited to, anatomical image information of the patient, segmentation information corresponding to the anatomical image information, and a dose map for the radiation treatment plan 105.

The anatomical image information can be in any of a variety of formats including two-dimensional and three-dimensional images (such as computed tomography (CT) images). This anatomical image information will typically include at least portions of the patient 107 including at least one treatment volume (such as a tumor) and one or more adjacent organs-at-risk or other patient structures.

The segmentation information identifies at least some of the anatomic structures (and their corresponding boundaries) in the foregoing anatomical image information. The segmentation information therefore serves, for example, to specifically identify such things as treatment volumes and discrete patient organs and/or other patient anatomical structures of interest.

For any number of reasons, the dose of radiation provided to various parts of any given patient structure is typically inconsistent and uneven. The aforementioned dose map indicates the spatial distribution of varying levels of radiation dose imparted to such patient structures. In the present case it is assumed that the dose map identifies quantitatively and discreetly differing levels of radiation dose within and throughout the segmented, identified patient structures.

The foregoing types of patient information are known in the art. Therefore, for the sake of brevity, further elaboration is not provided here in these specific regards.

At block 202, the control circuit 101 generates at least one organ-specific three-dimensional risk map as a function of the foregoing patient information.

By one approach the control circuit 101 is configured to generate this three-dimensional risk map by employing a neural network. As used herein, the expression "neural network" shall be understood to refer to an artificial neural network composed of artificial neurons or nodes. Such networks are known in the art and typically serve to solve any of a variety of artificial intelligence problems. These networks may be used for predictive modeling and are typically trained via a dataset.

These teachings will accommodate any of a variety of different neural networks. By one approach, and apropos of many relevant application settings, the neural network can comprise, at least in part, a convolutional neural network that often serves well when applied to the analysis of visual imagery. Convolutional neural networks are a type of deep neural network. (Convolutional neural networks are also known as shift invariant or space invariant artificial neural networks based on their shared-weights architecture and translation invariance characteristics.) Generally speaking, such a convolutional neural network can serve, at least in part, to extract features of interest from the patient information.

These teachings are highly flexible in practice. As one example in these regards, the neural network can include, in addition to a convolutional neural network, a recurrent neural network.

As another example in such regards, these teachings will accommodate employing a neural network that comprises, in part, a convolutional neural network and, in part, a fully-connected neural network. A fully-connected neural network includes fully-connected layers that connect every neuron in one layer to every neuron in another layer. Such a configuration can be particularly useful to classify the images being analyzed.

Pursuant to this process the convolutional neural network can be trained for at least one of a segmentation task and an auto-encoding task. By one approach the neural network can serve to predict the overall probability for a certain side effect. In that case the same neural network can then used to identify from which area of the input CT imagery this risk is originating from. The ordinarily-skilled person will appreciate that the neural network can therefore utilize transfer learning (in which case the already-trained network can be used as-is to extract general features or the network can be finetuned to, for example, extract features that are particularly specific to the present task) or, if desired, the neural network can be trained from scratch to predict the required outcome and risk map starting directly from the patient images (and hence without splitting the solution into feature selection followed by outcome prediction).

By another approach, such a convolutional neural network can be trained for at least one of a segmentation task and an auto-encoding task. The latter approaches are particularly helpful when pursuing a transfer learning type of approach. (Those skilled in the art will understand that transfer learning approaches serve to store knowledge gained while solving one problem and then applying it to a different but related problem.) Using this approach, the neural network can be one that was already trained for a specific task (such as auto-segmentation) but not necessarily for a follow-on but related task (such as feature extraction). That neural network can be leveraged to extract relevant features from the input images. Those features then become the input to another model (such as a neural network or some other machine learning approach of choice) that is then trained for the risk assessment task contemplated herein.

Generally speaking, the control circuit 101 can be configured to generate one or more organ-specific three-dimensional risk maps as a function of the aforementioned patient information by predicting at least one treatment outcome as a function of a set of defined treatment outcomes and the features extracted from the patient information. As used herein, these "defined treatment outcomes" are qualitative rather than quantitative. For example, rather than being a particular level of radiation dosage a defined adverse treatment outcome might be any of a variety of categorically qualitative (as versus quantitative) conditions such as "bleeding," "perforation," "dry mouth," "burning sensation," "redness," "irritation," "pain," "fibrosis," "hair loss," "irreversible loss of organ function," "blistering," "itchy skin," "dry skin," "sore gums," "difficulty swallowing," "coughing," "tooth decay," "fibrosis," "shortness of breath," "incontinence," "diarrhea," "erectile disfunction," "infertility," "osteoporosis," "secondary tumors," "neurological disorders," "arteriosclerosis," "locoregional recurrence," "distant metastasis" or "paralysis of extremities." That said, a specific treatment outcome such as "bleeding" can be further characterized in conjunction with, say, a particular quantified likelihood of occurring (for example, as a particular percentage likelihood such as 30% or 60%).

In addition to employing a neural network as described above, these teachings will also accommodate employing one or more non-neural network platforms to help predict the aforementioned treatment outcome. Useful examples of non-neural network platforms include, but are not limited to, random decision forest platforms and other machine learning methods such as support vector machines, logistic regression, or naïve Bayes classifier platforms.

The at least one organ-specific three-dimensional risk map so generated by the control circuit 101 visually highlights areas in a corresponding patient organ or other volumes of interest (such as the treatment volume) having a higher probability for an undesirable outcome prediction for the patient when administering the radiation treatment plan 105. The highlighted areas may be, for example, separate and discrete volumes within the corresponding patient volume. In such a case these separate and discrete volumes can be highlighted differently to indicate differing degrees of risk for an undesirable outcome.

The highlighting can vary with the needs and/or opportunities that correspond to a given application setting. By one approach the highlighting can utilize color. For example, different shades of a particular color (such as red) can serve to indicate varying degrees of predicted risk that pertain to the corresponding treatment outcome. As another example, different colors can serve to indicate varying degrees of predicted risk that pertain to the same corresponding treatment outcome. Other approaches to highlighting can of course be accommodated, including the use of any of a variety of icons, nomenclature, strobing, altered brightness, and so forth. By one approach the highlighting could include iso-risk lines (similar in concept to isodose lines).

By one approach the control circuit 101 generates a plurality of three-dimensional risk maps for each organ/volume of interest. Such an approach permits each risk map to be dedicated to only a particular categorical risk. For example, one such risk map can be dedicated to presenting only the predicted risk to various portions of the organ of interest with respect to bleeding that results from the radiation treatment plan as currently conceived.

Figure 3:
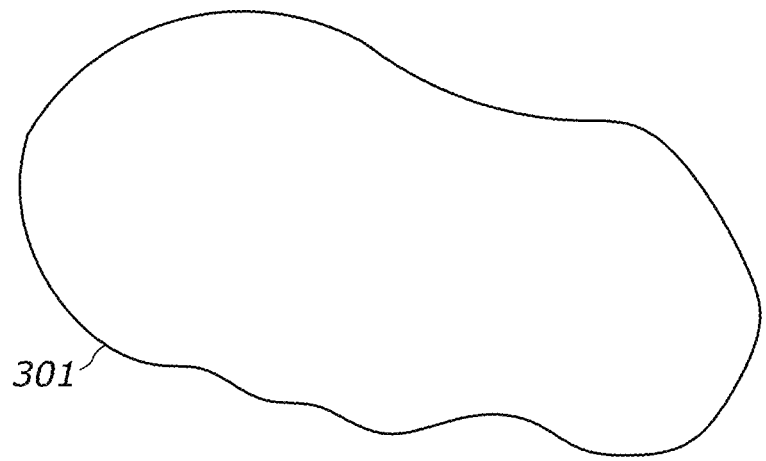
FIG. 3 comprises a schematic perspective view as configured in accordance with various embodiments of these teachings.
Figure 4:
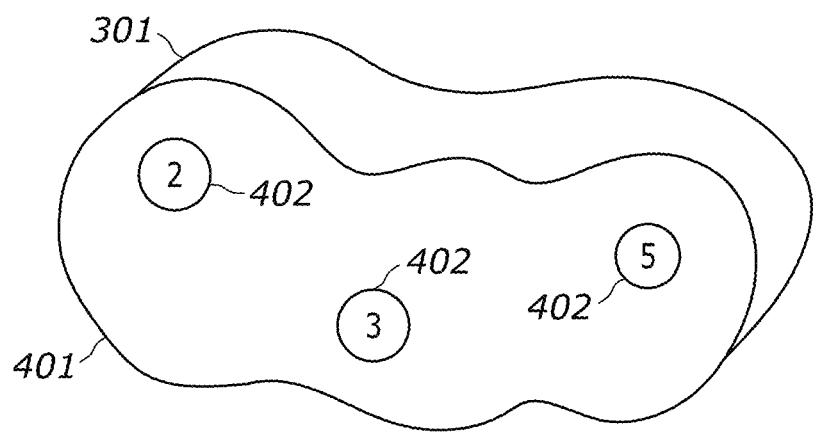
FIG. 4 comprises a schematic perspective sectioned view as configured in accordance with various embodiments of these teachings.
Figure 5:
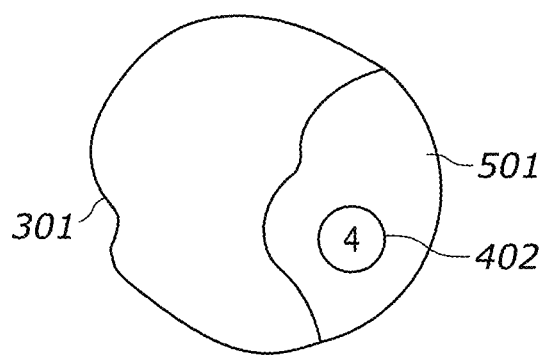
FIG. 5 comprises a schematic perspective sectioned view as configured in accordance with various embodiments of these teachings.

FIGS. 3 through 5 provides a simple illustrative example in these regards. FIG. 3 presents a schematic represented patient volume of interest 301. This patient volume of interest 301 may be, for example, a particular organ-at-risk. FIG. 4 presents a view of this patient volume of interest 301 that has been longitudinally sectioned 401 and which presents three different highlighted volumes 402. Each of these highlighted volumes 402 presents an inner volume where there is a higher risk of the adverse treatment outcome of interest. In this example each highlighted volume 402 includes a number. In this example, the higher the number the greater the predicted risk of the adverse outcome. FIG. 5 presents a view of the patient volume of interest 301 that has been laterally sectioned 501 and which presents another highlighted volume 402 that is located within the patient volume of interest 301.

Referring again to FIG. 2, at block 203 the control circuit 101 presents the generated at least one organ-specific three-dimensional risk map to a user via the aforementioned display 103. These teachings will accommodate permitting the user to manipulate the risk map as desired. Examples in these regards include, but are not limited to, enlarging part or all of the displayed risk map, rotating the risk map with respect to a particular axis, and sectioning the risk map as schematically represented in FIGS. 4 and 5 at any plane as specified by the user.

As noted above, these teachings are highly flexible in practice and will accommodate various modifications and/or supplemental activity. As but one example in these regards, gradient-weighted class activation mapping could be used to identify the areas from the patient imagery that contributed to a particular predicted outcome. As another example, in lieu of the above-referenced dose information (or in combination therewith) these teachings could instead utilize other useful metrics such as one that suitably describes a particular local biological impact of radiation on the patient volume of interest.

So configured, a technician can be easily and quickly informed about predicted adverse outcomes should the radiation treatment plan 105 be administered in its present form. That information, in turn, can potentially lead to the technician making further adjustments to the optimization of the radiation treatment plan 105 that may preserve the therapeutic efficacy of the treatment while avoiding certain adverse associated outcomes. These teachings do not rely upon the technician being sufficiently trained or experienced such that they could themselves mentally correlate a dose map to corresponding categorical risks in these regards.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method to facilitate assessing post-treatment adverse outcome risks associated with a not yet administered radiation treatment plan for a particular patient, the method comprising:
    by a control circuit:
        accessing patient information comprising at least:
            anatomical image information of the patient;
            segmentation information corresponding to the anatomical image information; and
            a dose map for the not yet administered radiation treatment plan;
        generating at least one organ-specific three-dimensional risk map as a function of the patient information, wherein the organ-specific three-dimensional risk map presents post-treatment categorical adverse results that are qualitative and that are due to radiation treatment administered per the radiation treatment plan should the not yet administered radiation treatment plan be administered;
        presenting the at least one organ-specific three-dimensional risk map to a user via a display.

2. The method of claim 1 wherein the control circuit is configured to generate the at least one organ-specific three-dimensional risk map as a function of the patient information by employing a neural network.

3. The method of claim 2 wherein the neural network comprises, at least in part, a convolutional neural network.

4. The method of claim 3 wherein the neural network comprises, in part, a convolutional neural network and, in part, a fully-connected neural network.

5. The method of claim 3 wherein the convolutional neural network is trained for at least one of:
    a segmentation task; and
    an auto-encoding task.

6. The method of claim 3 wherein the neural network further comprises, in part, a recurrent neural network.

7. The method of claim 3 wherein the convolutional neural network serves, at least in part, to extract features from the patient information.

8. The method of claim 7 wherein the control circuit is further configured to generate the at least one organ-specific three-dimensional risk map as a function of the patient information by predicting at least one treatment outcome as a function of a set of defined treatment outcomes and the features extracted from the patient information.

9. The method of claim 8 wherein the control circuit is configured to predict the at least one treatment outcome by employing at least one of:
a neural network; and
a non-neural network platform.

10. The method of claim 9 wherein the non-neural network platform comprises a random decision forest platform.

11. The method of claim 1 wherein the at least one organ-specific three-dimensional risk map visually highlights areas in a corresponding patient organ having a higher probability for an undesirable outcome prediction for the patient when administering the radiation treatment plan.

12. The method of claim 11 wherein the at least one organ-specific three-dimensional risk map visually highlights at least one discrete volume within the corresponding patient organ having a higher probability for an undesirable outcome prediction for the patient when administering the radiation treatment plan.

13. The method of claim 12 wherein the at least one organ-specific three-dimensional risk map visually highlights at least two separate and discrete volumes within the corresponding patient organ having a higher probability for an undesirable outcome prediction for the patient when administering the radiation treatment plan, wherein the at least two separate and discrete volumes are highlighted differently to indicate differing degrees of risk for an undesirable outcome.

14. The method of claim 1 wherein generating the at least one organ-specific three-dimensional risk map as a function of the patient information, wherein the organ-specific three-dimensional risk map presents post-treatment categorical adverse results that are qualitative comprises generating the at least one organ-specific three-dimensional risk map as a function of the patient information, wherein the organ-specific three-dimensional risk map presents post-treatment categorical adverse results that are qualitative rather than quantitative.

15. An apparatus to facilitate assessing post-treatment adverse outcome risks associated with a radiation treatment plan for a particular patient, the apparatus comprising:
a display;
a control circuit operably coupled to the display and configured to:
access patient information comprising at least:
anatomical image information of the patient;
segmentation information corresponding to the anatomical image information; and
a dose map for the not yet administered radiation treatment plan;
generate at least one organ-specific three-dimensional risk map as a function of the patient information, wherein the at least one organ-specific three-dimensional risk map presents post-treatment categorical adverse results that are qualitative rather than quantitative and that are due to radiation treatment administered per the radiation treatment plan should the not yet administered radiation treatment plan be administered; and
present the at least one organ-specific three-dimensional risk map to a user via the display.

16. The apparatus of claim 15 wherein the control circuit is configured to generate the at least one organ-specific three-dimensional risk map as a function of the patient information by employing a neural network.

17. The apparatus of claim 16 wherein the neural network is trained for at least one of:
a segmentation task; and
an auto-encoding task.

18. The apparatus of claim 16 wherein the neural network serves, at least in part, to extract features from the patient information.

19. The apparatus of claim 16 wherein the control circuit is further configured to generate the at least one organ-specific three-dimensional risk map as a function of the patient information by predicting at least one treatment outcome as a function of a set of defined treatment outcomes and the features extracted from the patient information.

20. The apparatus of claim 16 wherein the at least one organ-specific three-dimensional risk map visually highlights areas in a corresponding patient organ having a higher probability for an undesirable outcome prediction for the patient when administering the radiation treatment plan.

* * * * *